United States Patent [19]
Knittel et al.

[11] 3,980,535
[45] Sept. 14, 1976

[54] PROCESS FOR PRODUCING SULFONES
[75] Inventors: Dierk Knittel; Bertel Kastening, both of Julich, Germany
[73] Assignee: Kernforschungsanlage Julich Gesellschaft mit beschrankter Haftung, Julich, Germany
[22] Filed: May 29, 1974
[21] Appl. No.: 474,167

[30] Foreign Application Priority Data
June 2, 1973   Germany............................ 2328196

[52] U.S. Cl................................ 204/59 R; 204/72; 260/607 A
[51] Int. Cl.²..................... C25B 3/00; C07C 147/02
[58] Field of Search.......................... 204/59 R, 72; 260/607 AL

[56] References Cited
UNITED STATES PATENTS
3,344,047   9/1967   Neikam............................ 204/59 R OTHER PUBLICATIONS
Knittel et al., J. of Applied Electrochemistry, vol. 3, No. 4, pp. 291–296, 11/73.

*Primary Examiner*—F.C. Edmundson
*Attorney, Agent, or Firm*—Karl F. Ross; Herbert Dubno

[57] ABSTRACT

Sulfones are produced by reacting an organic compound R—X (where X is a substituent on the organic radical R replaceable by $SO_2^-$ ion) in an aprotic organic medium which may be the compound itself, with $SO_2^-$ ions produced by electrolysis upon introduction of sulfur dioxide into the system. Any of a wide range of sulfones or polysulfones having surfactant and fabric-treating (finishing) or therapeutic properties or serving as materials for the manufacture of plastics may be made in this manner.

4 Claims, 1 Drawing Figure

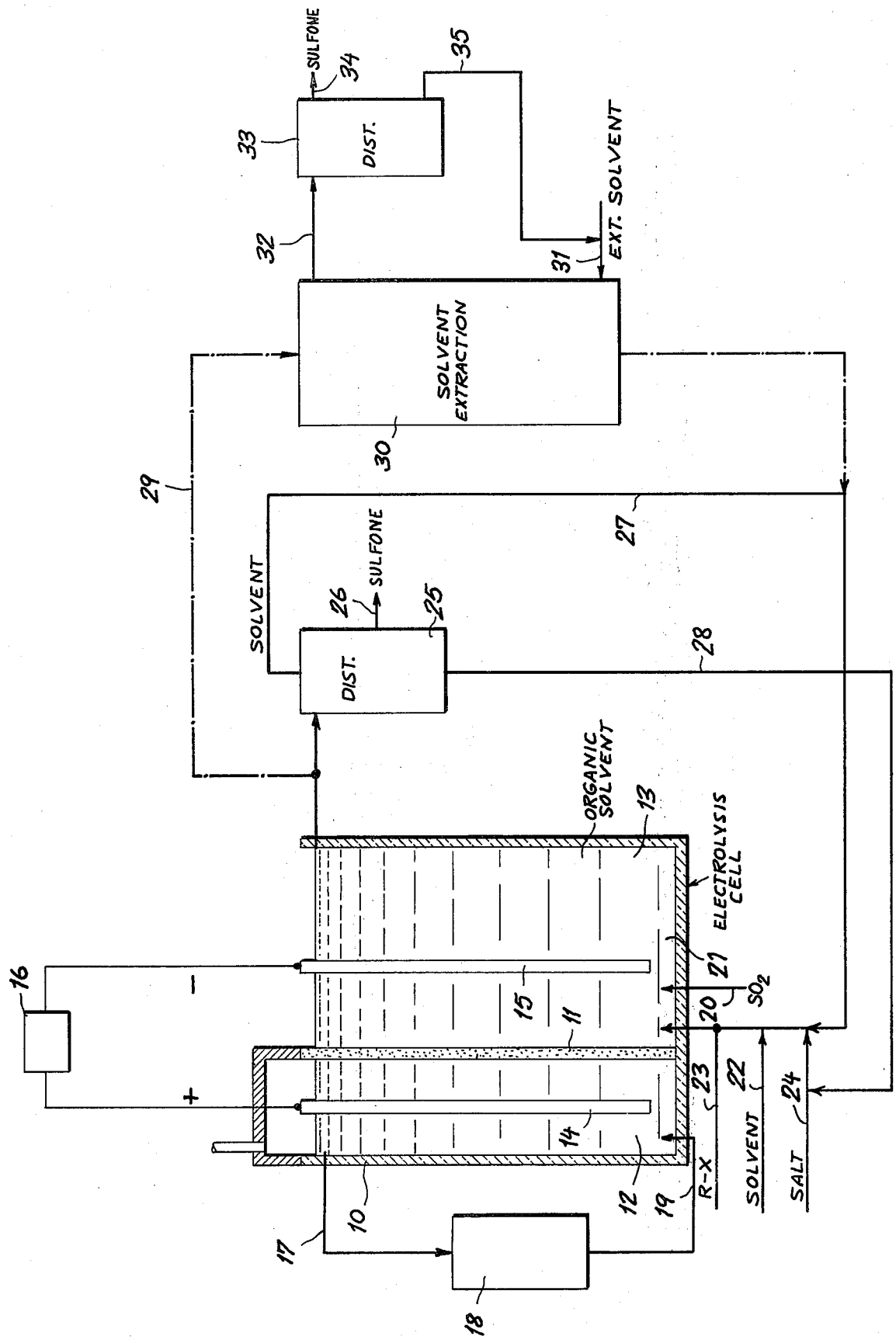

PROCESS FOR PRODUCING SULFONES

FIELD OF THE INVENTION

The present invention relates to a process for the production of sulfones or mixtures of sulfones.

BACKGROUND OF THE INVENTION

Sulfones are available for a wide variety of purposes and may be used in the manufacture of plastics in fabric finishing, as additives to textile fibers, as dyestuffs or adjuvants to dyestuffs and as therapeutic compounds in processes and treatments well known in the art.

Conventionally, sulfones may be made by several different techniques and generally it is possible to react an organic compound R—X with sodium sulfide to yield the organic sulfide R—S—R in accordance with the formula $$2R-X + Na_2S \rightarrow R-S-R + 2NaX$$

where X is a halogen atom, S is sulfur and R is the organic radical. The sulfide R—S—R is oxidized in a second stage to the sulfone with an oxidizing medium such as potassium permanganate or nitric acid or by catalytic systems. The oxidation may be represented by the simplified formula $$R-S-R + O_2 \rightarrow R-SO_2-R$$

where the reaction product R—SO$_2$—R is the sulfone. In accordance with the present invention, a process for the production of sulfones utilizes the fact that the SO$_2^-$ ion can replace certain functional groups of an organic compound in an organic medium (nonaqueous solvent) in which the SO$_2^-$ ion is formed by electrolysis.

The atoms or groups of a number of organic compounds have been found to be replaceable by SO$_2^-$ formed by electrolytic dissociation in an organic medium.

The present invention thus involves the steps of electrolyzing an organic medium containing sulfur dioxide (SO$_2$) to produce SO$_2^-$ ions in the presence of an organic compound R-X (or a group of such compounds) where R is an organic radical and X is an atom or group of atoms replaceable by SO$_2^-$, thereby resulting, after some secondary reactions, in R—SO$_2$—R.

The reaction is carried out in an aprotic organic solvent (nonaqueous medium) containing a salt, preferably a quaternary ammonium salt, designed to provide the necessary conductivity for the electrolysis current which transforms the SO$_2^-$ into SO$_2^-$. Preferably the salt is a tetra-alkyl ammonium salt such as tetramethyl or tetraethyl ammonium chloride or bromide.

The compounds R-X which are used in accordance with the present invention are preferably the organic halogen compounds, the sulfonic-acid esters and the sulfuric-acid esters although any compound capable of replacement of the group X by SO$_2^-$ may be employed.

According to the present invention, the organic compound is introduced into the medium or constitutes the reaction vehicle in which the sulfur dioxide is dissolved and the system is then subjected to electrolysis. Of course, a system in which the organic compound is in liquid form and can constitute the reaction medium or vehicle as well as one of the reactants, has the advantage that recovery of the sulfone is simplified. Organic compounds which can operate in this manner are dimethylsulfate, chloroacetonitrile and chloroacetone. The latter compounds require no separate solvent.

It has been found to be advantageous to prevent the electrolysis current from exceeding the maximum usable current density that produces only the SO$_2^-$ -ions. This can be accomplished by providing in the electrolysis cell a reference electrode which is not traversed by the electrolysis current and controlling the voltage between the reference electrode and the cathode so that with respect to the standard potential of the sulfur dioxide/sulfur dioxide anion REDOX couple (SO$_2$/SO$_2^-$), the potential does not exceed 0.1 volt. It has been found that best results are obtained when the sulfur dioxide concentration in the solution during electrolysis is at least 0.1 mole/liter.

The process of the present invention also has the significant advantage that it is possible to produce polymeric sulfones readily. It is only necessary, to this end, to use an organic compound having more than one halogen atom, i.e. a compound of the type X—R—X where R is a difunctional organic radical and X is an atom or group replaceable by SO$_2^-$. The reaction follows the overall formula $$2n(X-R-X) + 2n(SO_2) + 4ne^- \rightarrow \{R-SO_2\}_n + 4nX^-$$

where $n$ is an integer, $e^-$ is the electronic charge, R and X have their earlier-stated meanings and —(R—SO$_2$—R—SO$_2$)— is the repeating group of the polymer.

Of course, cyclic sulfones can also be produced from organic compounds having terminal X groups the C atoms to which they are attached being bridged by the —SO$_2$— group.

It has been found to be most advantageous to carry out the reaction in an electrolysis cell subdivided by a diaphragm or ion-exchange membrane into a cathode compartment and an anode compartment. When an anion ion-exchange membrane is used, the current through the cell is brought about solely by migration of the anions X$^-$ liberated by the cathodic process. The anions traverse the membrane and are oxidized at the anode. When X is a halogen atom, preferably chlorine or bromine, the halogen X$_2$ is liberated at the anode as the free halogen. The sulfone is formed in the cathode compartment. The system has been found to reduce side reactions which might tend to form impurities. A cell of the character described has been found to have an especially high yield of sulfones.

In the process of the present invention, the sulfones or sulfone mixtures can be separated from the solvent by distillation or by extraction with the extraction effluent then being distilled. For the extraction solvent, it is preferred to use a compound in which the salts (provided for conductivity) are insoluble. Such a solvent may be chloroform. The salt recovered in this manner may be recycled to the cell and even the free halogen may be used in ancillary chemical reactions.

BRIEF DESCRIPTION OF THE DRAWING

The above and other objects, features and advantages of the present invention will become more readily apparent from the following description, reference being made to the accompanying drawing in which the sole FIGURE is a flow diagram illustrating the invention.

SPECIFIC DESCRIPTION AND EXAMPLES

In the drawing, there is shown an electrolysis cell 10 which is subdivided by an anion exchange membrane 11 into an anode compartment 12 and a cathode compartment 13 respectively containing the anode 14 and the cathode 15. A source of a constant direct current 16 is connected across the electrodes 14, 15. The electrolyte contained in the anode compartment 12 is led at 17 to a halogen remover 18 where the halogen generated at the anode 14 is removed by extraction or distillation from the electrolyte, the latter being recycled at 19 to the anode compartment 12. Sulfur dioxide gas is introduced at 20 into the organic medium 21 within the cell, the medium consisting of a solvent introduced at 22; the organic compound R—X is introduced at 23 and the conductivity-producing salt is introduced at 24.

The reaction products are led into a distilling column 25 from which the sulfone is recovered at 26, solvent is recovered at 27 and recycled to the cell, and the salt is recovered at 28 and likewise recycled.

Alternatively, the reaction products may be led at 29 to a solvent-extraction column 30 into which the extraction solvent is introduced at 31. The extract is withdrawn at 32 and subjected to distillation at a column 33 to recover the sulfone at 34 and solvent at 35, the latter being recycled to the extraction stage.

EXAMPLE

Using a cell as illustrated in the drawing, dibutylsulfone is produced. The anode is glassy carbon and the cathode is platinum with an effective surface of 13 cm$^2$. Acetonitrile is used as the solvent and 0.2 moles/liter of tetraethylammonium-bromide is added as the conductivity-producing salt. The solvent is introduced into both the anode and cathode compartments. Sulfur dioxide is charged into the cathode compartment to a 5 molar concentration and n-butylbromide is charged into the cathode compartment. The butylbromide and sulfur dioxide concentrations are maintained substantially constant by metering additional quantities into the solution during the reaction. Electrolysis is carried out at a constant current density of 38.5 mA/cm at a temperature of 80°C.

After 10,000 coulombs have passed, electrolysis is terminated and the solvent is separated from the reaction product in the cathode compartment by distillation. The residue is shaken with water and chloroform and the mixture is permitted to stand to separate a chloroform phase from the aqueous phase. The aqueous phase contains the salt and the chloroform phase is fractionally distilled to recover the product.

We claim:

1. A process for the production of a sulfone, comprising the steps of:
   a. introducing into an electrolysis cell, subdivided by an anion-exchange membrane or a diaphragm into an anode compartment and a cathode compartment, a reaction system consisting essentially of an aprotic organic solvent having dissolved therein a conductivity-promoting salt, $SO_2$, and an organic component selected from the group which consists of an organic halogen compound in which the halogen is chlorine, bromine, or iodine;
   b. maintaining the $SO_2$ concentration in said system at least at 0.1 moles/liter;
   c. electrolyzing said system in said cell at a current density, temperature and voltage sufficient to form $SO_2^-$-ions from the $SO_2$ of said system and effecting a reaction of the $SO_2^-$ with said component in said cathode compartment to form the corresponding organic sulfone therein; and
   d. preventing the electrolysis current from exceeding the maximum current density for production of $SO_2^-$ by providing in the electrolysis cell a reference electrode not traversed by the electrolysis current and controlling the voltage between the reference electrode and the cathode so that with respect to the standard potential of the $SO_2/SO_2^-$ redox couple the potential does not exceed 0.1 volt.

2. The process defined in claim 1 wherein said $SO_2^-$ ions are first formed in said solvent either inside or outside said cathode, before said organic component is introduced into the same.

3. The process defined in claim 1 wherein $SO_2$ and said organic component are dissolved in said solvent prior to electrolysis of said system.

4. The process defined in claim 1 wherein said organic solvent and said organic component are the same substance.

* * * * *